(12) United States Patent
Kraft

(10) Patent No.: US 10,478,565 B2
(45) Date of Patent: Nov. 19, 2019

(54) ASSEMBLY FOR A DRUG DELIVERY DEVICE AND DRUG DELIVERY DEVICE

(71) Applicant: Sanofi-Aventis Deutschland GMBH, Frankfurt am Main (DE)

(72) Inventor: Torsten Kraft, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 230 days.

(21) Appl. No.: 15/029,337

(22) PCT Filed: Nov. 10, 2014

(86) PCT No.: PCT/EP2014/074147
§ 371 (c)(1),
(2) Date: Apr. 14, 2016

(87) PCT Pub. No.: WO2015/071212
PCT Pub. Date: May 21, 2015

(65) Prior Publication Data
US 2016/0271334 A1    Sep. 22, 2016

(30) Foreign Application Priority Data
Nov. 15, 2013 (EP) ..................... 13193024

(51) Int. Cl.
*A61M 5/315* (2006.01)
(52) U.S. Cl.
CPC .... *A61M 5/31568* (2013.01); *A61M 5/31551* (2013.01); *A61M 5/31585* (2013.01); *A61M 2205/581* (2013.01); *A61M 2205/582* (2013.01)
(58) Field of Classification Search
CPC .................... A61M 2205/582; A61M 5/31551
See application file for complete search history.

(56) References Cited

U.S. PATENT DOCUMENTS

| 533,575 A | 2/1895 | Wilkens |
| 5,226,895 A | 7/1993 | Harris |

(Continued)

FOREIGN PATENT DOCUMENTS

| CN | 103260674 | 8/2013 |
| CN | 103260675 | 8/2013 |

(Continued)

OTHER PUBLICATIONS

International Search Report and Written Opinion in International Application No. PCT/EP2014/074147, dated Feb. 2, 2015, 10 pages.

(Continued)

*Primary Examiner* — Bhisma Mehta
*Assistant Examiner* — Matthew A Engel
(74) *Attorney, Agent, or Firm* — Fish & Richardson P.C.

(57) ABSTRACT

An assembly (100) for a drug delivery device is presented. The assembly comprising a housing, a clicker member (2) and a clutch member (1) comprising a rotatable clutch feature (20). The assembly further comprises a counter clicker (8) which is configured to interact with the clicker member (2) to form a clicker mechanism, and a spring element (3) arranged between the clicker member (2) and the clutch member (1), the spring element (3) being arranged to move the clutch member (1) towards the first position and away from the clicker member (2) away from each other. The assembly (100) is further configured such that the clutch member (1) is axially movable with respect to the housing between a first position and a second position different from the first position, wherein, when the clutch member (1) is rotated in the first position with respect to the clicker member (2), the counter clicker (8) rotates with respect to the clicker member (2) and, when the clutch member (1) is (Continued)

in the second position, a rotation of the clutch member (1) with respect to the clicker member (2) is prevented.

19 Claims, 5 Drawing Sheets

(56) References Cited

U.S. PATENT DOCUMENTS

| | | | |
|---|---|---|---|
| 5,279,586 A | | 1/1994 | Balkwill |
| 5,304,152 A | | 4/1994 | Sams |
| 5,320,609 A | | 6/1994 | Haber et al. |
| 5,383,865 A | | 1/1995 | Michnel |
| 5,480,387 A | | 2/1996 | Gabriel et al. |
| 5,505,704 A | | 4/1996 | Pawelka et al. |
| 5,582,598 A | | 12/1996 | Chanoch |
| 5,626,566 A | | 5/1997 | Petersen et al. |
| 5,674,204 A | * | 10/1997 | Chanoch ............ A61M 5/31535 604/207 |
| 5,688,251 A | | 11/1997 | Chanoch |
| 5,921,966 A | | 7/1999 | Bendek |
| 5,961,495 A | | 10/1999 | Walters et al. |
| 6,004,297 A | | 12/1999 | Steenfeldt-Jensen et al. |
| 6,193,698 B1 | | 2/2001 | Kirchhofer |
| 6,221,046 B1 | | 4/2001 | Burroughs et al. |
| 6,235,004 B1 | | 5/2001 | Steenfeldt-Jensen |
| 6,248,095 B1 | | 6/2001 | Giambattista et al. |
| 6,899,698 B2 | | 5/2005 | Sams |
| 6,936,032 B1 | | 8/2005 | Bush et al. |
| 7,241,278 B2 | | 7/2007 | Moller |
| 2002/0052578 A1 | | 5/2002 | Moller |
| 2002/0120235 A1 | | 8/2002 | Enggaard |
| 2003/0050609 A1 | | 3/2003 | Bernard |
| 2004/0059299 A1 | | 3/2004 | Moller |
| 2004/0210199 A1 | * | 10/2004 | Atterbury ......... A61M 5/31535 604/224 |
| 2004/0260247 A1 | * | 12/2004 | Veasey .............. A61M 5/31551 604/207 |
| 2004/0267207 A1 | | 12/2004 | Veasey et al. |
| 2005/0113765 A1 | | 5/2005 | Veasey et al. |
| 2006/0153693 A1 | | 7/2006 | Fiechter |
| 2008/0234633 A1 | * | 9/2008 | Nielsen ................ A61M 5/24 604/208 |
| 2009/0264828 A1 | * | 10/2009 | Dette ................. A61M 5/24 604/189 |
| 2009/0275914 A1 | * | 11/2009 | Harms .................. A61M 5/24 604/506 |
| 2009/0275916 A1 | * | 11/2009 | Harms .................. A61M 5/24 604/506 |
| 2010/0324493 A1 | * | 12/2010 | Plumptre .......... A61M 5/31541 604/207 |
| 2010/0331788 A1 | * | 12/2010 | Plumptre .......... A61M 5/31543 604/207 |
| 2010/0331790 A1 | * | 12/2010 | Plumptre .......... A61M 5/31511 604/207 |
| 2010/0331792 A1 | * | 12/2010 | Plumptre .......... A61M 5/31525 604/207 |
| 2013/0197478 A1 | * | 8/2013 | Leak ................. A61M 5/31525 604/506 |
| 2013/0289518 A1 | * | 10/2013 | Butler .............. A61M 5/31535 604/500 |
| 2016/0265533 A1 | | 9/2016 | Veasey et al. |
| 2016/0287806 A1 | * | 10/2016 | Kraft ................ A61M 5/31568 |

FOREIGN PATENT DOCUMENTS

| | | |
|---|---|---|
| CN | 103260676 | 8/2013 |
| EP | 0937476 | 1/2005 |
| EP | 0937471 | 9/2005 |
| GB | 20030004822 | 3/2003 |
| GB | 20030004823 | 3/2003 |
| WO | WO 1999/038554 | 8/1999 |
| WO | WO 2001/010484 | 2/2001 |
| WO | WO02/092153 | 11/2002 |
| WO | WO 2011/039208 | 4/2011 |
| WO | WO 2011/051366 | 5/2011 |
| WO | WO2011/154489 | 12/2011 |
| WO | WO 2012/049139 | 4/2012 |
| WO | WO 2012/049140 | 4/2012 |
| WO | WO 2012/049141 | 4/2012 |
| WO | WO2012/130705 | 10/2012 |

OTHER PUBLICATIONS

International Preliminary Report on Patentability in International Application No. PCT/EP2014/074147, dated May 17, 2016, 8 pages.
Rote Liste, "50. Hypophysen-, Hypothalamushormone, andere regulatorische Peptide u. ihre Hemmstoffe," Chapter 50, ed. 2008, 20 pages.

* cited by examiner

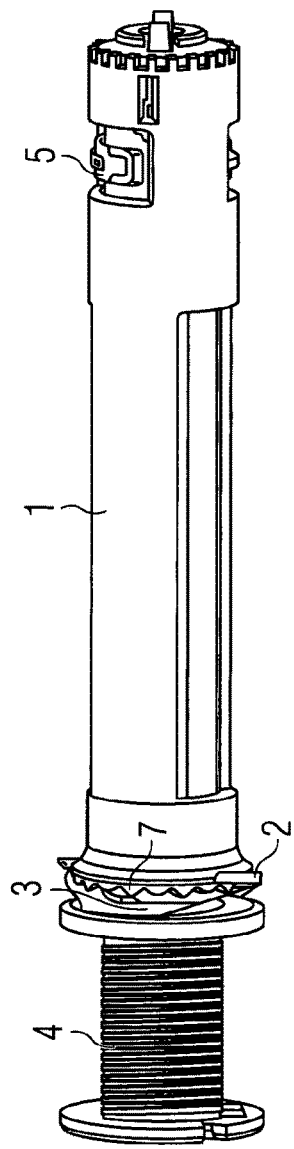
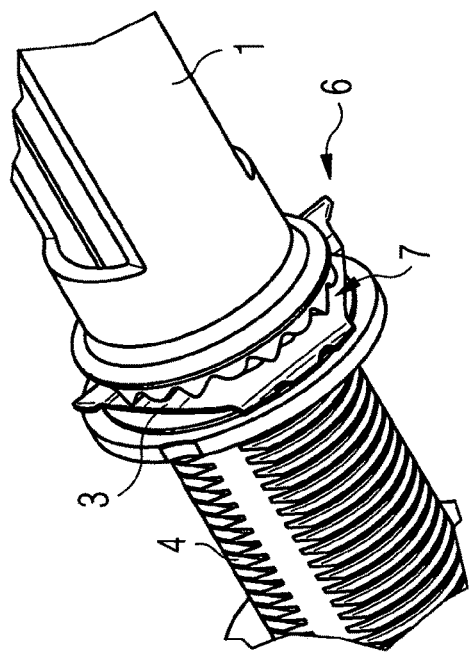

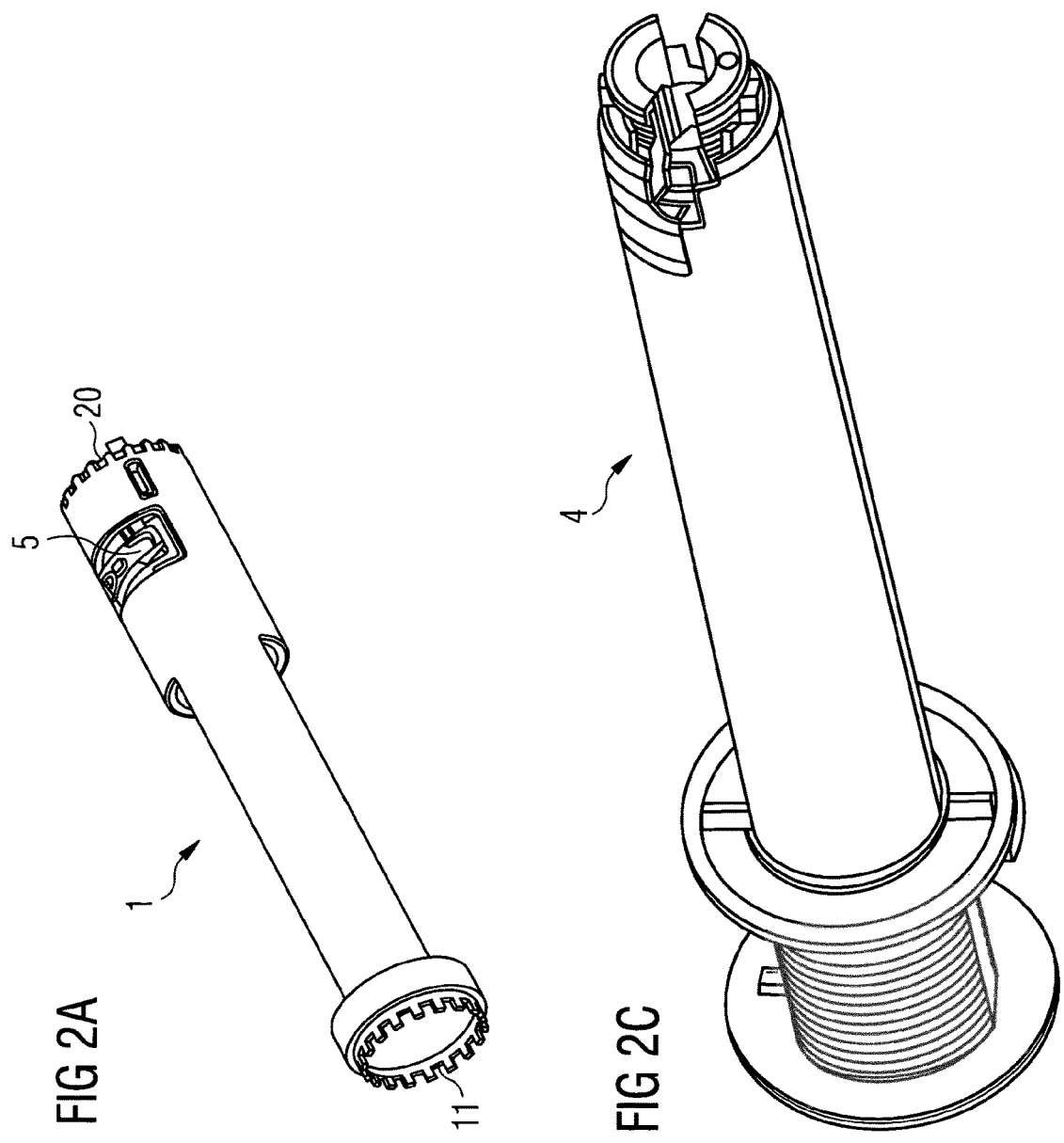
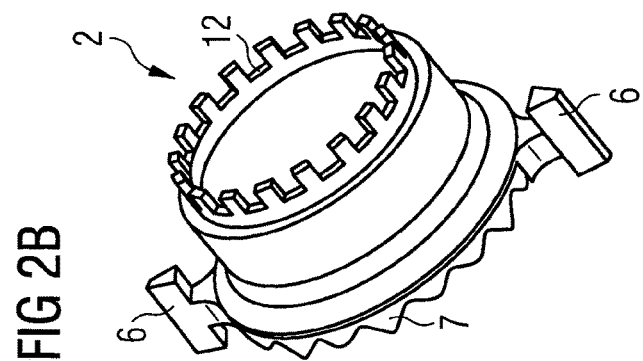

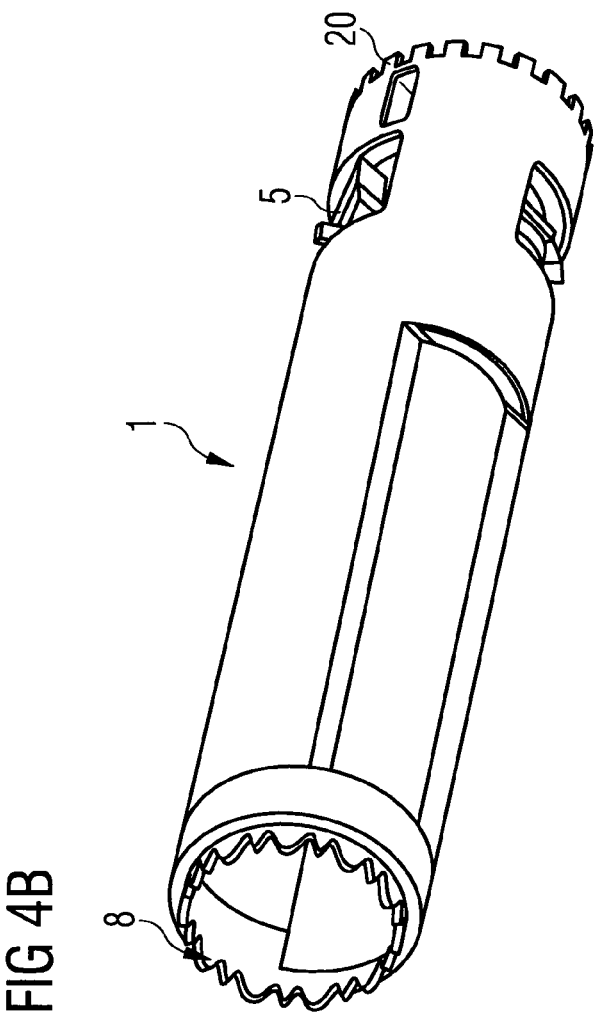
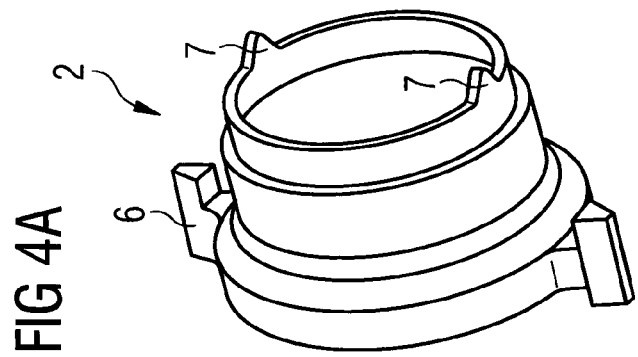

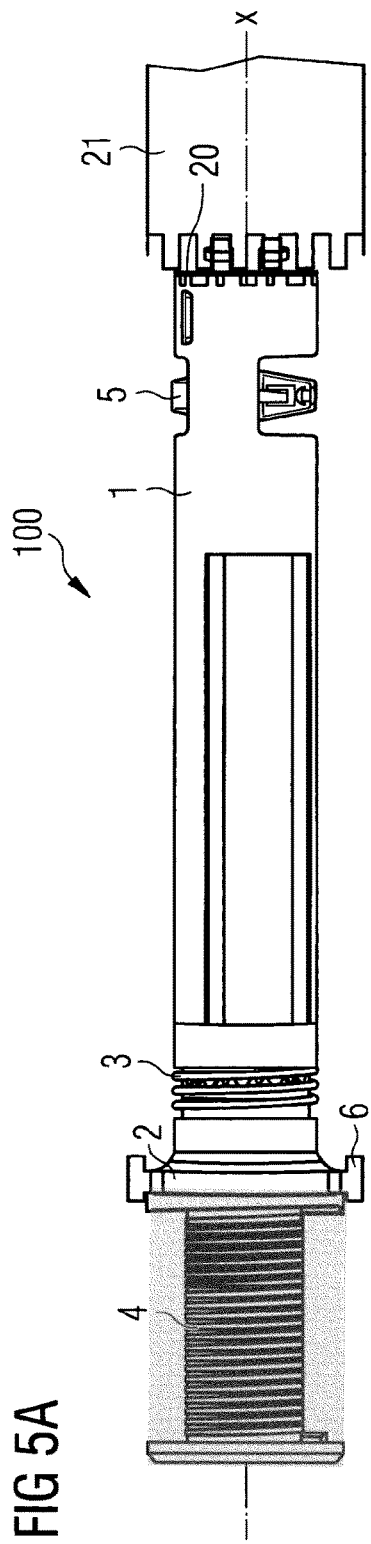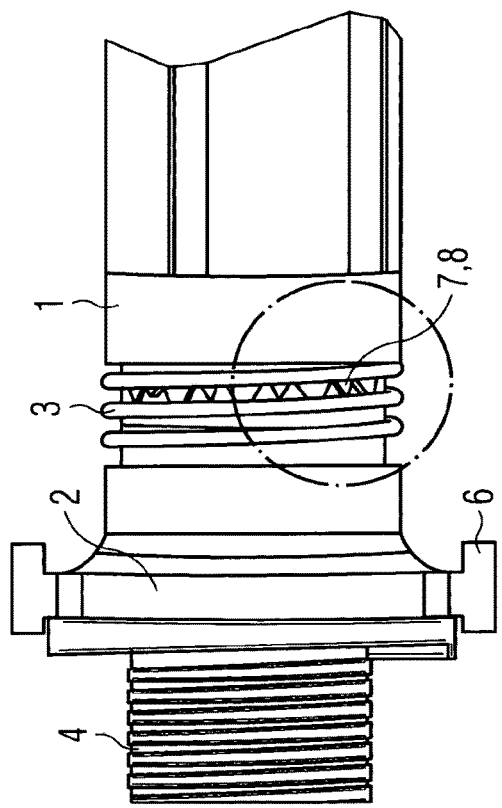
FIG 5A
FIG 5B

ASSEMBLY FOR A DRUG DELIVERY DEVICE AND DRUG DELIVERY DEVICE

CROSS-REFERENCE TO RELATED APPLICATIONS

This application is a U.S. national stage application under 35 USC § 371 of International Application No. PCT/EP2014/074147, filed on Nov. 10, 2014, which claims priority to European Patent Application No. 13193024.0, filed on Nov. 15, 2013, the entire contents of which are incorporated herein by reference.

The present disclosure relates to an assembly for a drug delivery device such as an injector-type device and a drug delivery device.

Implementations of the present disclosure can provide an assembly by which a drug delivery device can be improved. Particularly, with the assembly, the drug delivery device can be rendered more user-friendly and/or robust.

The subject-matter of the independent claim 1 can be implemented to provide an assembly for a drug delivery device. Advantages embodiments and refinements are subject-matter of the dependent claims.

One aspect of the present disclosure relates to an assembly for a drug delivery device comprising a housing. The housing may comprise a main axis. The assembly further comprises a clicker member. The clicker member may be rotationally locked with respect to the housing. The clicker member is, preferably, axially moveable with respect to the housing only within certain limits. The main axis may be a longitudinal axis of the housing. The assembly further comprises a clutch member, comprising a clutch feature. The clutch feature is, preferably, rotatable. The clutch feature may be configured to interact with a further clutch member, e.g. of the assembly or the drug delivery device. The assembly further comprises a counter clicker which is configured to interact with the clicker member to form a clicker mechanism.

The assembly is, furthermore, configured such that the clutch member is axially moveable with respect to the housing between a first position and a second position being different from the first position. The first position may relate to a position of the clutch member in which a dose of a drug may be set by a user of the assembly or the drug delivery device. The second position may relate to a position of the clutch member in which a dose is actually dispensed or after a dose has been dispensed from the assembly or the drug delivery device. The first position and the second position of the clutch member may relate to different axial positions of the clutch member with respect to the housing.

The assembly further comprises a spring element which is arranged between the clicker member and the clutch member. The spring element may be retained between the clicker member and the clutch member. The spring element is arranged to move the clutch member towards the first position and away from the clicker member.

The assembly is configured such that, when, in the first position, the clutch member is rotated with respect to the clicker member, the counter clicker rotates with respect to the clicker member and a clicking action is performed, wherein, when the clutch member is in the second position, a rotation of the clutch member with respect to the clicker member and therewith a rotation of the counter clicker with respect to the clicker member is prevented, and a clicking action is not performed.

As an advantage, problems concerning a fixation of the spring element, e.g. with respect to the housing may be avoided by the presented assembly concept. For instance, when extensive force or torque is applied to the clutch member, e.g. during maloperation of the assembly or the device by the user, it can be avoided that components of the assembly are pulled out of its bearing or fixation. Thus, a particular robust design can be presented. Moreover, the presented design complies with a clutch functionality which may be crucial for the functioning of drug delivery devices (see below).

In an embodiment, the clicker member comprises a clicker feature which is configured to interact with the counter clicker to form the clicker mechanism, when the clutch member is in the first position.

One aspect relates to a drug delivery device comprising the assembly.

The clicker mechanism is, preferably, a setting clicker mechanism, i.e. a clicker mechanism operated, e.g. during a dose setting operation of the assembly and/or the drug delivery device.

In an embodiment, the clicker mechanism is disposed to provide for an audible and/or tactile feedback to the user, when the clutch member is rotated with respect to the housing, and when the clutch member is in the first position.

In an embodiment, the clicker member and/or the clutch member are configured sleeve-like. As an advantage, the clutch member and the clicker member may be guided in the housing of the assembly and the clicker mechanism and a clutch engagement (see below) may be embodied robust.

In an embodiment, the assembly comprises a further clutch member and the assembly is configured such that, when the clutch member is in the first position, a clutch engagement which can be established between the clutch feature and the further clutch member is engaged and, when the clutch member is in the second position, the clutch engagement is released. For instance, the clutch engagement is configured to form a rotational locking between the clutch member and the further clutch member. As an advantage, a relative rotation between the clutch member and said component can be prevented, whereas this rotation and/or prevention may be crucial for an operation of the assembly and/or the drug delivery device.

In an embodiment, the assembly comprises in addition to the clicker mechanism a feedback mechanism comprising a feedback member. The assembly is configured such that the feedback mechanism can be operated in the second position of the clutch member, whereby the feedback member exerts a torque on the clutch member. The assembly is, preferably, configured such that, when the clutch member is in the second position, the feedback mechanism is operated automatically and provides an audible and/or tactile feedback to a user of the assembly and/or the drug delivery device, preferably during dispensing of a dose of drug. The feedback member may be a dose dial sleeve or any other component.

In an embodiment, the feedback member is the further clutch member, and the assembly is configured such that, when the clutch member is in the second position, the torque is too small as to effect relative rotational movement of the clicker member and the clutch member. As an advantage of this embodiment, the clicker member and the clutch member may axially also not be separated by the feedback mechanism, when the clutch member is in the second position.

In an embodiment, the clicker feature and the counter clicker feature each comprise or constitute teeth which are spaced around a circumference of the clicker member and the component comprising the counter clicker. According to this embodiment, it is achieved that a relative rotation of the clicker member and the counter clicker may at least partly be converted into an axial movement of the clicker member or the counter clicker with respect to the respective other component. In general, the clicker mechanism can be embodied easily, in this way.

In an embodiment, the clicker mechanism is configured such that it can only be operated or activated when the clutch member is in the first position.

In an embodiment, the assembly comprises a drive sleeve being coupled to a piston rod of the assembly. The drive sleeve is, furthermore, rotationally locked with respect to the clutch member. The drive sleeve and/or the piston rod may constitute the drive sleeve and a piston rod of the drug delivery device, respectively. The drive sleeve is further rotationally locked with respect to the clutch member. This embodiment may, particularly be expedient when the assembly is applied in the drug delivery device.

In an embodiment the drive sleeve extends through the clicker member and the clutch member. According to this embodiment a robust functionality of the drug delivery device may be achieved easiest, as the drive member may be required to interact with further components of the assembly or the drug delivery device beyond the axial extension of the clutch member and/or the clicker member.

In an embodiment, the clicker member is rotationally secured with respect to the housing and the counter clicker is coupled to the clutch member such that the counter clicker and the clutch member co-rotate when in the first position, the clutch member is rotated with respect to the clicker member.

In an embodiment, the counter clicker is provided by the drive sleeve and the assembly is configured such that the clicker feature and the counter clicker feature are arranged facing each other. This embodiment allows, expediently, an interaction between the counter clicker and the clicker member in order to form the clicker mechanism.

In an embodiment, the clicker member and the clutch member are configured to interact via a coupling which is suitable to rotationally lock the clicker member and the clutch member when the clutch member is in the second position. The rotational locking of the clicker member and the clutch member may be advantageous, as, when the clutch member is in a second position, the above-mentioned torque exerted on the clutch member by the feedback mechanism may tend to relatively rotate the clutch member and the clicker member. Said rotation can, in summary, be avoided by means of said coupling.

In an embodiment, the assembly is configured such that, during an operation of the clicker mechanism, the clicker member and the clutch member are axially moved with respect to each other in a limited fashion, and wherein, when the clutch member is in the first position, the axial distance of the movement by which the clicker member is moved relative to the clutch member or vice versa is less than the axial distance between the first position and the second position of the clutch member. According to this embodiment it can, expediently, be prevented that the mentioned coupling is released during an operation of the clicker mechanism.

In an embodiment, the counter clicker is provided by the clutch member and the assembly is configured such that the clicker feature and the counter clicker feature are arranged facing each other. This embodiment allows, expediently, an interaction between the counter clicker and the clicker feature in order to form the clicker mechanism.

During the mentioned relative axial movement between the clicker member and the clutch member, the spring element is, preferably, either biased or relaxed, e.g. when the teeth of the clicker feature and those of the counter clicker move over or pass by one another.

The term "drug", as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39), des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Features which are described herein above and below in conjunction with different aspects or embodiments, may also apply for other aspects and embodiments. Further features and advantageous embodiments of the subject-matter of the disclosure will become apparent from the following description of the exemplary embodiment in conjunction with the figures, in which:

FIG. 1A shows an assembly which is not in accordance with the present disclosure.

FIG. 1B shows a perspective view of the assembly of FIG. 1A in greater detail.

FIG. 2A shows a perspective view of a clutch member.

FIG. 2B shows a perspective view of a clicker member.

FIG. 2C shows a perspective view of a drive sleeve.

FIG. 4A shows a perspective view of the clicker member according to an alternative embodiment.

FIG. 4B shows a perspective view of a clutch member according to an alternative embodiment.

FIG. 5A shows a side view of an alternative embodiment of an assembly according to the present disclosure.

FIG. 5B shows a side view of the assembly of FIG. 5A in greater detail.

Figure 3A:
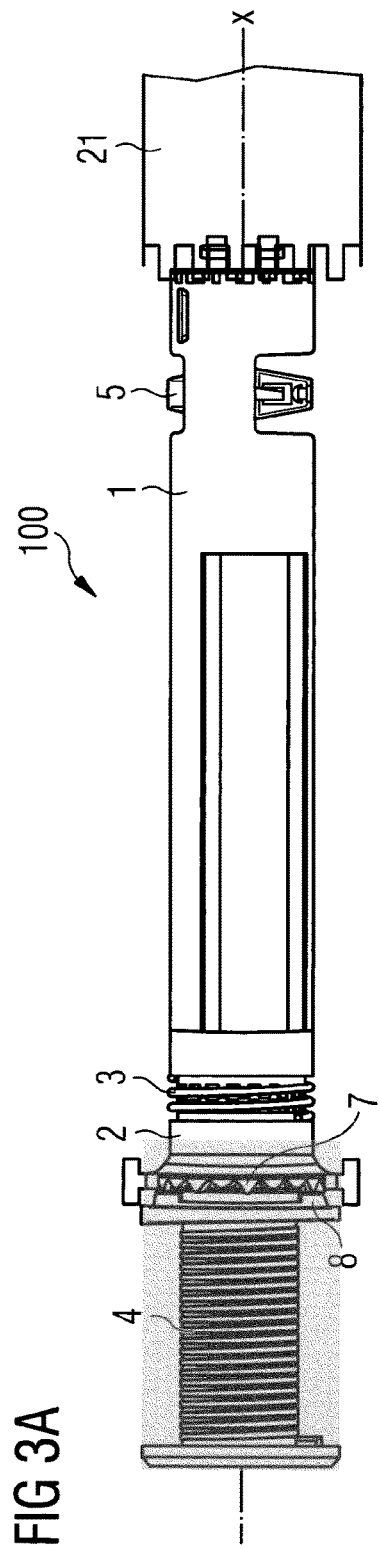
FIG. 3A shows a side view of a first embodiment of an assembly according to the present disclosure.

Like elements, elements of the same kind and identically acting elements may be provided with the same reference numerals in the figures. Additionally, the figures may be not true to scale. Rather, certain features may be depicted in an exaggerated fashion for better illustration of important principles.

FIG. 1A shows an assembly which is not in accordance with the present disclosure. The assembly comprising a clutch member 1. The clutch member 1 comprises an elongate shape. The distal end (left end in FIG. 1) of the clutch member 1 comprises a clicker feature 7. The clicker feature 7 may be or comprise teeth or a tooth interface. The left side in FIGS. 1A and 1B may relate to a distal end of the assembly 100 while the right side may relate to a proximal end of the assembly. The clutch member 1 is further configured sleeve-like. The assembly further comprises a spring element 3. The spring element 3 is a leave spring. The spring member 3 is rotationally locked with respect to the housing. The spring element 3 comprises a counter clicker (not explicitly indicated), e.g. comprising teeth, wherein the counter clicker feature is configured to interact with the clicker feature 7 to form a clicker mechanism. The clicker mechanism may be suitable to provide for an audible and/or tactile feedback, when, e.g. during setting of a dose of drug, the clutch member 1 is rotated with respect to the spring element 3. The assembly 100 further comprises a drive sleeve 4. The drive sleeve 4 is, preferably, arranged to extend at least partly through the clutch member 1.

The spring element 3 shown in FIGS. 1A and 1B may cause problems concerning its fixation in a housing (not explicitly indicated). For instance, when extensive force or torque is applied to the clutch member 1 during setting or dispensing of a dose of drug, the spring element 3 may be pulled out of its bearing or fixation.

The "distal end" of the assembly or the drug delivery device or a component thereof shall mean the end which is closest to the dispensing end of the drug delivery device.

The "proximal end" of the assembly or the drug delivery device or a component thereof shall mean the end which is furthest away from the dispensing end of the drug delivery device.

The clutch member 1 further comprises a feedback mechanism, such as a dispense clicker 5 at its proximal end, the dispense clicker 5 may comprise a resilient arm. The resilient arm (not explicitly indicated) may be deflected radially inwardly when a further component e.g. of the assembly is rotated relative to the clutch member 1 (see below).

Parts of the assembly of FIG. 1A are shown in FIG. 1B. In FIG. 1B, the clutch member 1 is arranged in a first axial position, e.g. with respect to the housing which is not explicitly indicated. It is further shown that the spring element 3 comprises protrusions 6 which serve the purpose for axially locking the spring element 3 with respect to the housing. When the clutch member 1 is rotated relative to the spring member 3, the clicker feature 7, preferably, clicks over the counter clicker 8 of the spring element 3 such that an audible or tactile feedback is provided to the user. Said clicking or feedback is, preferably, facilitated by the resiliency of the spring element 3. The mentioned rotation may relate to a dose setting or dialing operation of the assembly 100 or a corresponding drug delivery device, wherein the assembly 100 may be applied.

When the clutch member 1 is moved distally (second axial position), i.e. to the left in FIG. 1B with respect to the drive sleeve 4, the spring member 3 is biased and the counter clicker 8 is prevented from moving with respect to the clutch member 1 in order to interact with the clicker features 7 in the clicker mechanism.

FIG. 2A shows a perspective view of a clutch member 1 in accordance with the present disclosure in a first embodiment. At its distal end, the clutch member 1 comprises teeth 11 for forming a coupling 10 (see FIG. 3B below). The clutch member 1 further comprises a clutch feature 20 at a proximal end of the clutch member 1 (right end in FIG. 2A). The clutch feature 20 may be configured to interact with a further clutch member 21 (schematically indicated in FIGS. 3A and 5A) of the assembly 100 or the drug delivery device to form a clutch mechanism and/or engagement. For instance, the clutch engagement is configured to form a rotational locking between the clutch member 1 and the further clutch member 21. The clutch feature 20 may, as depicted, comprise a toothed surface along a circumference of the clutch member 1, wherein each tooth comprises longitudinally arranged side edges.

According to FIG. 1A, the clutch member 1 further comprises the dispense clicker 5.

FIG. 2B shows a perspective view of a clicker member 2 in accordance with the present disclosure and according to the first embodiment. The clicker member 2 comprises teeth 12 of the coupling 10 matching with the teeth 11 of the clutch member 1. According to FIG. 1B, the clicker member 2 comprises the protrusions 6.

FIG. 2C shows a drive sleeve 4 in a perspective view and in accordance with the present disclosure. The drive sleeve 4 comprises an elongate shape such that it may at least partly extend through, e.g. the clicker member 2, the spring element 3 and/or the clutch member 1. The drive sleeve 4, preferably, interacts with further components of an assembly or a drug delivery device, such as a piston rod. Preferably, the drive sleeve 4 is coupled to the piston rod of the assembly 100 (cf. FIG. 3A), e.g. for dispensing of a dose of drug from a device in which the assembly 100 is applied. The drive sleeve 4 is, furthermore, rotationally locked with respect to the clutch member 1.

FIG. 3A shows a side view of a first embodiment of an assembly 100 according to the present disclosure. Although a complete drug delivery device may not be shown in the figures, implementations of the present disclosure may relate to such a drug delivery device comprising the assembly 100 shown in FIGS. 2 to 5. The assembly 100 comprises a longitudinal axis X.

In contrast to the assembly shown in FIGS. 1A and 1B, the assembly 100 comprises the clutch member 1 (cf. FIG. 2A) and the clicker member 2 (cf. FIG. 2B). The clicker member 2 comprises the clicker feature 7. In contrast to FIGS. 1A and 1B, the counter clicker 8 is further provided by the drive sleeve 4, particularly at a proximal face of the drive sleeve 4. Accordingly, the clicker feature 7 is provided at a distal end of the clicker member 2. The clicker features 7 and the counter clicker 8 both comprise teeth which match in order to provide for the clicker mechanism. The teeth of the counter clicker 8 may constitute a counter clicker feature (not explicitly indicated). Between the clicker member 2 and the clutch member 1, a spring element 3, particularly a spiral spring, is arranged or retained. The spring element 3 is arranged or retained between the clutch member 1 and the clicker member 2 in a biased state. The spring element 3 tends to move the clutch member 1 and the clicker element 2 away from each other. The clutch member 1 is shown arranged in a first axial position, e.g. relative to the housing. In this position, the above-mentioned clutch engagement is engaged. In FIG. 3A, a further clutch member 21, as a separate component of the assembly 100 is shown. The further clutch member 21 preferably comprises—like the clutch feature 20—a circumferentially disposed, toothed surface (not explicitly indicated), which is configured to interact with that one of the clutch feature 20 for forming the clutch engagement. The further clutch member 21 may be a dose dial sleeve of the assembly, and contribute to the dispense clicker 5 (see below).

The further clutch member 21 may be a dose dial sleeve which is provided outside of the clutch member 1 and radially inward of the housing. When the desired dose has been dialed or set, the user may dispense this dose by depressing an activation button (not explicitly indicated), for example. This displaces the clutch member 1 axially with respect to the further clutch member 21 from the first (axial) position to the second (axial) position, wherein the mentioned clutch mechanism is released. The drive sleeve 4, the clutch member 1 and the further clutch member 21 may then rotate together with respect to the housing. Furthermore, by the interaction of the teeth of the clicker feature 7 and the counter clicker 8, the clutch member 1 and with it the drive sleeve 4 may be hindered from being rotated with respect to the housing. However, the drive sleeve 4 may be axially moved with respect to the housing and the assembly 100 may be configured such that the longitudinal axial movement of the drive sleeve 4 causes a piston rod of the assembly or the device to rotate, thereby advancing a piston in a cartridge to dispense a dose of drug.

Figure 3B:
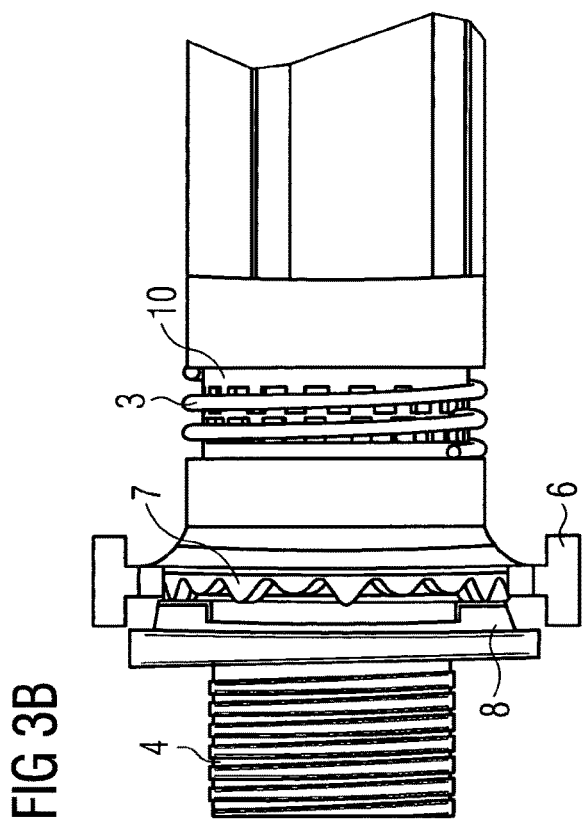
FIG. 3B shows a side view of the assembly of FIG. 3A in greater detail.

In FIG. 3B, a portion of the assembly 100 of FIG. 3A is shown in greater detail. The teeth 11 of the clutch member 1 and the teeth 12 of the clicker member 2 are configured to form a coupling 10 which allows relative rotation of the clicker member 2 and the clutch member 1 when the clutch member 1 is in the first position and which prevents relative rotation of said components when the clutch member 1 is in the second position. The teeth 11, 12 of the coupling 10 are configured and shaped accordingly, i.e. they comprise no slopes like the teeth of the clicker feature 7 and/or the counter clicker 8 but comprise edges which extend parallel to the longitudinal axis X.

When, in the described first position of the clutch member 1, the clutch member 1 is rotated with respect to the housing or with respect to e.g. the drive sleeve 4, the clicker mechanism is activated as described above and the spring element 3 is biased when e.g. a tooth of the clicker feature 7 moves over or passes a tooth of the counter clicker 8. Thereby, the clutch member 1 and/or the clicker member 2 may be retained or borne within the assembly 100 such that a relative axial movement of the mentioned components at least within certain limits is possible. Preferably, the clicker member 2 is retained between the clutch member 1 or, as the case may be, the spring element 3 and the drive sleeve 4.

During the operation of the clutch mechanism, i.e. when e.g. a tooth of the clicker feature 7 passes or moves over a tooth of the counter clicker (cf. description of FIGS. 1A and 1B), the clicker member 2 is, preferably, moved proximally, i.e. to the right with respect to the clutch member 1 (cf. FIG. 3A) against the resilience of the spring element 3.

When the clutch member 1 is moved from the first axial position to the second axial position, the spring element 3 is biased and the teeth of the clicker feature 7 and the counter clicker 8 engage such that a rotation of the clutch member 1 with respect to the clicker member 2 is hindered or prevented.

The assembly 100 further comprises a feedback mechanism formed by the dispense clicker 5 of the clutch member 1 and a feedback member being separate from the clutch member 1. The feedback member is preferably the further clutch member 21 (not explicitly indicated in FIG. 3B) of the assembly 100 or the device, for example. Preferably, the feedback mechanism comprises the further clutch member 21 (cf. FIG. 3A). When the clutch member 1 is in the second position, a torque is, preferably, exerted on the clutch member 1 by the feedback mechanism. Said torque may account for the feedback that is provided by the feedback member which may rotate with respect to the clutch member 1. Said torque is, preferably too small, as to effect a relative rotational movement of the clicker member 2 and the clutch member 1. Due to the tooth engagement, a further torque may be necessary to move the clicker member 2 and the clutch member 1 axially away from each other, whereas the further torque is then greater than the mentioned torque.

The assembly 100 is further configured such that, when the clutch member 1 is in the first position, the axial distance by which the clicker member 2 is moved relative to the clutch member 1 or vice versa is less than a relative axial distance of the clutch member 1 and the clicker member 2 which is necessary to engage the coupling 10.

FIG. 4A shows a perspective view of the clicker member 2 of an alternative embodiment of the assembly 100 in accordance with the present disclosure. It is shown that—in contrast to the embodiment shown in FIG. 2B for example—a proximal end face of the clicker member 2 comprises the clicker feature 7 as opposingly arranged teeth. The two depicted teeth each comprise oblique (e.g. with respect to a longitudinal axis of the clicker member 2) or sloped side faces which are configured to interact with the counter clicker 8 to form the clicker mechanism.

FIG. 4B shows a perspective view of the clutch member 1 according to the embodiment of FIG. 4A. The clutch member 1 comprises at its distal end (left in FIG. 4B) teeth of the counter clicker 8. Said teeth are configured to interact with the teeth of the clicker feature 7 during an operation of the clicker mechanism. The teeth further extend over the whole circumference of the clutch member 1. The clutch member 1 further comprises the clutch feature 20 at a proximal end of the clutch member 1 (right end in FIG. 4B).

FIG. 5A shows an assembly 100 according to the embodiments shown in FIGS. 4A and 4B. In contrast to the embodiment shown in FIGS. 2A, 2B, 2C and 3A, 3B, no coupling is provisioned here. The coupling may be dispensable here, as the rotational locking between the clutch member 1 and the clicker member 2 (in the second position of the clutch member 1) is adopted by the teeth of the clicker mechanism, i.e. the teeth of the clicker feature 7 and those of the counter clicker 8. According to FIG. 3A, the clutch member 1 is depicted in the first position and, thus, the clutch engagement between the clutch member 1 and the further clutch member 21 is engaged.

This is shown also in greater detail in FIG. 5B showing a portion of the assembly 100 of FIG. 5A in greater detail. Again, the spring element 3 is arranged between the clutch member 1 and the clicker member 2 in order to tend to urge said components away from each other.

During the operation of the clutch mechanism according to this embodiment, a tooth of the clicker feature 7 may, preferably, also pass over a tooth of the counter clicker (cf. operation explained above). Then, the clicker member 2 is, preferably moved distally, i.e. to the left with respect to the clutch member 1 (cf. FIG. 5A) against the resilience of the spring element 3. Alternatively, the clutch member 1 may then be moved proximally, i.e. to the right with respect to the clicker member 2.

In addition to the protrusions 6, further fixation means may be provisioned, whereby a securing of the clutch member 2 with respect to the housing can be achieved.

According to the concept of the present disclosure, the spring element, advantageously, adopts a double functionality, as it firstly enables the clicker functionality, wherein it tends to separate the clutch member 1 and the clicker member 2 and, secondly, it enables the functionality of the clutch mechanism between the clutch member 1 and the further clutch member, wherein the spring element tends to hold the mentioned components in the clutch engagement.

The scope of protection is not limited to the examples given herein above. The invention is embodied in each novel characteristic and each combination of characteristics, which particularly includes every combination of any features which are stated in the claims, even if this feature or this combination of features is not explicitly stated in the claims or in the examples.

REFERENCE NUMERALS

1 Clutch member
2 Clicker member
3 Spring element
4 Drive sleeve
5 Dispense clicker
6 Protrusion
7 Clicker feature
8 Counter clicker
10 Coupling
11, 12 Teeth
20 Clutch feature
21 Further clutch member
100 Assembly
X Longitudinal axis

The invention claimed is:

1. An assembly for a drug delivery device, the assembly comprising:
   a housing;
   a rotatable clutch member of an elongate shape, the clutch member comprising a clutch feature at a proximal end of the clutch member and teeth at a distal end of the clutch member, wherein the clutch member is axially movable with respect to the housing between a first position and a second position different from the first position;
   a further clutch member, wherein the assembly is configured such that,
      when the clutch member is in the first position, a clutch engagement established between the clutch feature and the further clutch member is engaged, and
      when the clutch member is in the second position, the clutch engagement is released;
   a clicker member comprising teeth matching the teeth of the clutch member, the teeth of the clicker member and the teeth of the clutch member forming a coupling between the clutch member and the clicker member;
   a counter clicker configured to interact with the clicker member to form a clicker mechanism; and
   a spring element arranged between the clicker member and the clutch member, the spring element arranged to move the clutch member towards the first position and away from the clicker member so that the clutch member is rotatable with respect to the clicker member, wherein the assembly is configured such that,
   when the clutch member is in the first position, the clutch member is rotated with respect to the clicker member and the counter clicker rotates with respect to the clicker member, and
   when the clutch member is in the second position, a rotation of the clutch member with respect to the clicker member is prevented by the coupling.

2. The assembly according to claim 1, further comprising a feedback mechanism comprising a dispense clicker and a feedback member, wherein the further clutch member acts as the feedback member, and wherein the assembly is configured such that the feedback mechanism can be operated in the second position of the clutch member, whereby the feedback member exerts a torque on the clutch member.

3. The assembly according to claim 2, wherein the assembly is configured such that, when the clutch member is in the second position, the torque is insufficient for effecting relative rotational movement of the clicker member and the clutch member.

4. The assembly according to claim 1, further comprising a drive sleeve coupled to a piston rod of the assembly and rotationally locked with respect to the clutch member.

5. The assembly according to claim 4, wherein the drive sleeve extends through the clicker member and the clutch member.

6. The assembly according to claim 4, wherein the clicker member comprises a clicker feature and the counter clicker comprises a counter clicker feature, wherein the counter clicker is provided by the drive sleeve, and wherein the assembly is configured such that the clicker feature and the counter clicker feature are arranged facing each other.

7. The assembly according to claim 1, wherein the clicker member comprises a clicker feature and the counter clicker comprises a counter clicker feature, wherein the counter clicker is provided by the clutch member, and wherein the assembly is configured such that the clicker feature and the counter clicker feature are arranged facing each other.

8. The assembly according to claim 1, wherein the coupling is suitable to rotationally lock the clicker member and the clutch member when the clutch member is in the second position.

9. The assembly according to claim 1, wherein the assembly is configured such that, during an operation of the clicker mechanism, the clicker member and the clutch member are axially moved with respect to each other within certain limits, and
   wherein, when the clutch member is in the first position, an axial distance of relative movement between the clicker member and the clutch member is less than an axial distance between the first position and the second position of the clutch member.

10. The assembly according to claim 1, wherein the clicker member is rotationally secured with respect to the housing and the counter clicker is coupled to the clutch member such that the counter clicker and the clutch member co-rotate when, in the first position, the clutch member is rotated with respect to the clicker member.

11. A drug delivery device comprising:
   an assembly comprising:
      a housing;
      a rotatable clutch member of an elongate shape, the clutch member comprising a clutch feature at a proximal end of the clutch member and teeth at a distal end of the clutch member, wherein the clutch member is axially movable with respect to the housing between a first position and a second position different from the first position;
      a further clutch member, wherein the assembly is configured such that,
         when the clutch member is in the first position, a clutch engagement established between the clutch feature and the further clutch member is engaged, and
         when the clutch member is in the second position, the clutch engagement is released;
      a clicker member comprising teeth matching the teeth of the clutch member, the teeth of the clicker member and the teeth of the clutch member forming a coupling between the clutch member and the clicker member;
      a counter clicker configured to interact with the clicker member to form a clicker mechanism; and
      a spring element arranged between the clicker member and the clutch member, the spring element arranged to move the clutch member towards the first position and away from the clicker member so that the clutch member is rotatable with respect to the clicker member,
   wherein the assembly is configured such that,
      when the clutch member is in the first position, the clutch member is rotated with respect to the clicker member and the counter clicker rotates with respect to the clicker member, and
      when the clutch member is in the second position, a rotation of the clutch member with respect to the clicker member is prevented by the coupling.

12. The device according to claim 11, wherein the assembly further comprises a feedback mechanism comprising a feedback member, wherein the further clutch member acts as the feedback member, and wherein the assembly is configured such that the feedback mechanism can be operated in the second position of the clutch member, whereby the feedback member exerts a torque on the clutch member.

13. The device according to claim 12, wherein the assembly is configured such that, when the clutch member is in the second position, the torque is insufficient for effecting relative rotational movement of the clicker member and the clutch member.

14. The device according to claim 11, wherein the assembly further comprises a drive sleeve coupled to a piston rod of the assembly and rotationally locked with respect to the clutch member.

15. The device according to claim 14, wherein the drive sleeve extends through the clicker member and the clutch member.

16. The device according to claim 14, wherein the clicker member comprises a clicker feature and the counter clicker comprises a counter clicker feature, wherein the counter clicker is provided by the drive sleeve, and wherein the assembly is configured such that the clicker feature and the counter clicker feature are arranged facing each other.

17. The device according to claim 11, wherein the clicker member comprises a clicker feature and the counter clicker comprises a counter clicker feature, wherein the counter clicker is provided by the clutch member, and wherein the assembly is configured such that the clicker feature and the counter clicker feature are arranged facing each other.

18. The device according to claim 11, wherein the coupling is suitable to rotationally lock the clicker member and the clutch member when the clutch member is in the second position.

19. The device according to claim 11, further comprising a cartridge connected to the housing, the cartridge carrying a drug consisting of at least one pharmaceutically active compound, wherein the assembly is configured to advance a piston in the cartridge to dispense a dose of the drug.

* * * * *